United States Patent [19]

Suzuki

[11] Patent Number: 5,072,458
[45] Date of Patent: Dec. 17, 1991

[54] VEST FOR USE IN AN AMBULATORY PHYSIOLOGICAL EVALUATION SYSTEM INCLUDING CARDIAC MONITORING

[75] Inventor: Arata Suzuki, Ramsey, N.J.

[73] Assignee: Capintec, Inc., Ramsey, N.J.

[21] Appl. No.: 395,082

[22] Filed: Aug. 17, 1989

Related U.S. Application Data

[60] Continuation-in-part of Ser. No. 96,521, Sep. 15, 1987, Pat. No. 5,007,427, which is a continuation-in-part of Ser. No. 46,854, May 7, 1987, Pat. No. 4,920,969, which is a division of Ser. No. 785,549, Oct. 8, 1987, abandoned.

[51] Int. Cl.⁵ .................... A41D 1/04; A61B 5/04
[52] U.S. Cl. .......................................... 2/102; 2/94; 128/659
[58] Field of Search .............. 2/44, 92, 94, 95, 102, 2/100, 96; 128/659, 653 R

[56] References Cited

U.S. PATENT DOCUMENTS

| 245,655 | 8/1881 | Phelps | 2/44 |
|---|---|---|---|
| 317,474 | 5/1885 | Strouse | 2/44 |
| 1,475,072 | 11/1923 | Langerman | 2/102 |
| 1,739,112 | 12/1929 | Wisbrod | 2/102 |
| 2,156,504 | 5/1939 | Liss | 2/102 |
| 2,810,912 | 10/1957 | Kaufman | 2/102 |
| 3,529,307 | 9/1970 | Belson et al. | 2/94 |
| 4,508,110 | 4/1985 | Modglin | 2/44 |
| 4,602,387 | 7/1986 | Zakrzewski | 2/102 |
| 5,007,427 | 4/1991 | Suzuki | 2/102 |

FOREIGN PATENT DOCUMENTS

| 372501 | 5/1932 | United Kingdom | 2/102 |
|---|---|---|---|
| 950488 | 2/1964 | United Kingdom | 2/102 |

Primary Examiner—Werner H. Schroeder
Assistant Examiner—Amy Brooke Vanatta
Attorney, Agent, or Firm—Fleit, Jacobson, Cohn, Price, Holman & Stern

[57] ABSTRACT

A vest for use in an ambulatory physiological evaluation system for holding cardiac monitoring equipment in position relative to the heart of a patient. The vest comprises a chest member having first and second detachable side members. The side members can be positioned relative to each other at the front of the vest via slots in each of the side members. An additional coupling means detachably and adjustably joins the side members at the back of the vest. A mounting bracket assembly is provided on the front of the vest for receiving a radiation detector. The vest includes horizontal slots to mount the mounting bracket thereto. Vertical slots are provided in the mounting bracket for receiving screw clamps which pass through both the vertical slots in the mounting bracket and the horizontal slots in the vest to allow positioning of the mounting bracket relative to the vest. The mounting bracket includes further adjustable plates which allow further adjustable positioning of the radiation detector relative to the mounting bracket.

7 Claims, 5 Drawing Sheets

VEST FOR USE IN AN AMBULATORY PHYSIOLOGICAL EVALUATION SYSTEM INCLUDING CARDIAC MONITORING

This application is a continuation-in-part of application Ser. No. 096,521 filed Sept. 15, 1987, which is a continuation-in-part of Application Ser. No. 046,854 filed May 7, 1987, which is a Divisional of application Ser. No. 785,549 filed Oct. 8, 1987, which is now abandoned.

FIELD OF THE INVENTION

The present invention relates to a vest for supporting detectors such as radionuclide detectors, for physiological parameters. The vest is worn by a patient and used in an evaluation system employing nuclear medicine to monitor and diagnose a patient's physiological activities with the radionuclide detectors and miniature electronics.

BACKGROUND OF THE INVENTION

From statistics taken from the American Heart Association, it is known that over 40 million Americans have some form of heart and/or blood vessel disease. Over one million deaths occur annually due to cardiovascular disease, and over 600,000 deaths are the result of coronary artery disease. Accurate diagnosis and appropriate therapy are critical to the management of a patient with cardiovascular disease.

Many diagnostic tools are available to diagnose coronary artery disease or heart attack. These include blood tests, electrocardiograms (resting or during stress, angiography (conventional and digital subtraction techniques), ultrasound and nuclear cardiology techniques. The nuclear cardiology techniques, which employ nuclear imaging, are the only techniques capable of functional assessment of the heart. Nuclear cardiology techniques are capable of detecting infarctions, ischemia, coronary artery disease, assessment of birth defects and predicting effectiveness of cardiac medications and/or surgical intervention.

Relative to other diagnostic imaging techniques, nuclear imaging has several important advantages which account for its current growth. Most important, nuclear imaging can provide diagnostic information related to cardiac function rather than just anatomy. By utilizing radioactive tracers, nuclear imaging of left ventricular function (LVF) can monitor physiological processes over time, whereas most other imaging methods can produce only a static picture. Therefore, the use of radionuclides in diagnosis of cardiovascular disease is continually expanding.

In addition to the diagnostic imaging procedure, an important need exists for a device which permits nuclear and ECG measurements to be made in an ambulatory mode. This need exists because, during the performance of ordinary activities associated with daily living, left ventricular function varies over a wide range in both the healthy and diseased heart. These changes in left ventricular function, brought about by such ordinary activities as walking, climbing stairs, physiological stress, exposure to severe temperature changes, etc., may equal or exceed those observed in a laboratory during the performance of a nuclear cardiac dynamic function study. In coronary artery disease, the accurate and continuous measurement of changes in cardiac physiology such as ischemia, arrhythmia, fall in ejection fraction, or a rise in relative cardiac blood volume can assist in the management of the patient's disease. In addition, measurements made before and after surgery or drug therapy may offer additional insights into the impact of these treatments on left ventricular function or dysfunction.

Likewise, in silent ischemia (also defined by many cardiologists as left ventricular dysfunction), where electrocardiographic changes may possibly be observed after several minutes of ECG recording, left ventricular function changes may be observed in a matter of seconds after the onset of the decompensation. The effective monitoring of these left ventricular changes (such as, increase in end systolic volume) result in better design and administration of a proper therapy regime.

An example of a nuclear cardiac probe designed to meet the need for noninvasive evaluation of rapidly developing flanges in global left ventricular function is discussed in "The Nuclear Cardiac Probe," by Dr. Henry N. Wagner, Jr., *Hospital Practice*, April 1982, Volume 17, Number 4, pages 163–177. The probe discussed in the article is housed in a console which may be moved by casters from place to place. The probe, however, does not offer a system that can be easily carried by the patient.

Ambulatory monitoring of left ventricular function has been shown to be possible with the development of a miniaturized system of radionuclide detectors and electronics incorporated into a vestlike garment and worn outside the chest. See, for example, "An Ambulatory Ventricular Function Monitor: Validation and Preliminary Clinical Results," by Drs. Wilson, Sullivan, Moore, Zielonka, Alpert, Boucher, McKusick and Strauss, The American Journal of Cardiology, Sept. 1, 1983, Volume 52, pages 601–606.

A truly ambulatory cardiac evaluation system has several potential areas of application. Firstly, it may be particularly useful in evaluating the incidence of silent ischemia. There is now tremendous interest in the cardiology community in the idea that many of the episodes of myocardial ischemia in patients with coronary disease are probably pain free. There has been much talk that ST segment changes seen on Holter recordings may represent ischemia. That, however, has been extremely controversial because people are aware of other circumstances where ST segment changes are not caused by ischemia. Therefore, the issue has been to identify changes in vertricular function which could be caused by ischemia in association with the ST changes. This has been something which is very difficult to identify in ambulatory subjects. The present invention can make these measurements at the same time.

The second application is to define the impact of drug therapy. This is particularly important in patients who have just been diagnosed as having coronary disease, hypertension or some other circumstances where there is a need to know whether the drug therapy has depressed the patients ventricular function. The patient can be studied before and after taking the drug. In both cases, the patient pursues his/her daily activities to see whether the drug has negatively impacted cardiac function. Currently this is done by merely monitoring the patients reaction—do they feel tired, get out of breath, etc.

The third area is to define the appropriate exercise prescription in both people who do not have known heart disease, but are just out of shape, and in people who have known heart disease. It is particularly useful on patients after they have had a myocardial infarction where the patient should begin exercising on a gradual basis so that they do not exercise to a point where their ventricular function diminishes.

Thus, there is still a need for an ambulatory evaluation system which can be worn in relative comfort by a patient for monitoring coronary artery disease, in surgical and post-operative workups, for anesthesia rehabilitation, for monitoring exercise regime, for drug and diet studies, and for monitoring the effectiveness of drug administered in the therapeutic program. The present invention is directed toward filling that need.

SUMMARY OF THE INVENTION

The present invention relates to a vest made of a flexible plastic material, such as "Aquaplast", which contains a pattern of ventilation holes. The vest is adapted to be worn on the torso of a human and contains an arrangement of shoulder straps to provide for a snug, yet relatively comfortable fit. The vest is worn to provide a base to which a cardiac monitor including a main detecting device is attached and held in a precise relationship between the main detecting device and an anatomical body, such as the left ventricle of the heart.

Attachment of the cardiac monitor to the vest is accomplished through the use of a detector mounting bracket which is a lightweight, formed, metallic structure with means for attaching to both the vest and to the detecting device.

In order to properly align the detector mounting bracket relative to the left ventricle of the heart, an alignment fixture is used prior to mounting the main detector to the mounting bracket. The detector alignment fixture basically comprises a planar leveling plate to which is fastened a plate within which is embedded a centerline cursor made from lead elements. The detector alignment fixture is mounted to the face of the detector mounting bracket with four cap screws. The mounting bracket also has a pair of opposed flanges which aid in mounting the centerline plate. After mounting, the detector alignment fixture is centered on the detector mounting plate.

A conventional scintillation or gamma camera is brought up to the alignment fixture and adjusted for parallelism. The picture derived from the camera on a cathode-ray tube (CRT) display shows the position of the cursor relative to the left ventricle of the heart. If the centerline of the cursor is within 10 millimeters of the desired position, any further adjustment can be made by the sliding mechanism of the radiation detector mounting bracket. If the location of the centerline is further away from the left ventricle of the heart than 10 millimeters, the mount must be readjusted relative to the vest or the vest garment relative to the patient and the above procedure repeated.

In another embodiment of the invention a modified mounting bracket structure is provided which incorporates a ball-type socket carried on a mounting plate and into which the alignment fixture can be releasably clamped for use with a gamma camera to set the positioning of the socket, after which the socket, thus set, can be used to mount a main detector. This embodiment provides somewhat greater flexibility of adjustment.

Thus, it is the primary object of the present invention to provide a truly ambulatory physiological evaluation system including cardiac monitoring.

It is another object of the present invention to provide a mounting apparatus for mounting a radiation detector in a precise relationship to a interior organ of the body of a patient.

It is a further object of the present invention to provide an apparatus to facilitate mounting of a radiation detector to an ambulatory vest in a precise relationship with the left ventricle of the heart of the wearer of the vest.

Other objects, advantages, and features will become apparent by reference to the following detailed description and drawings.

DETAILED DESCRIPTION OF THE DRAWINGS

Figure 1:
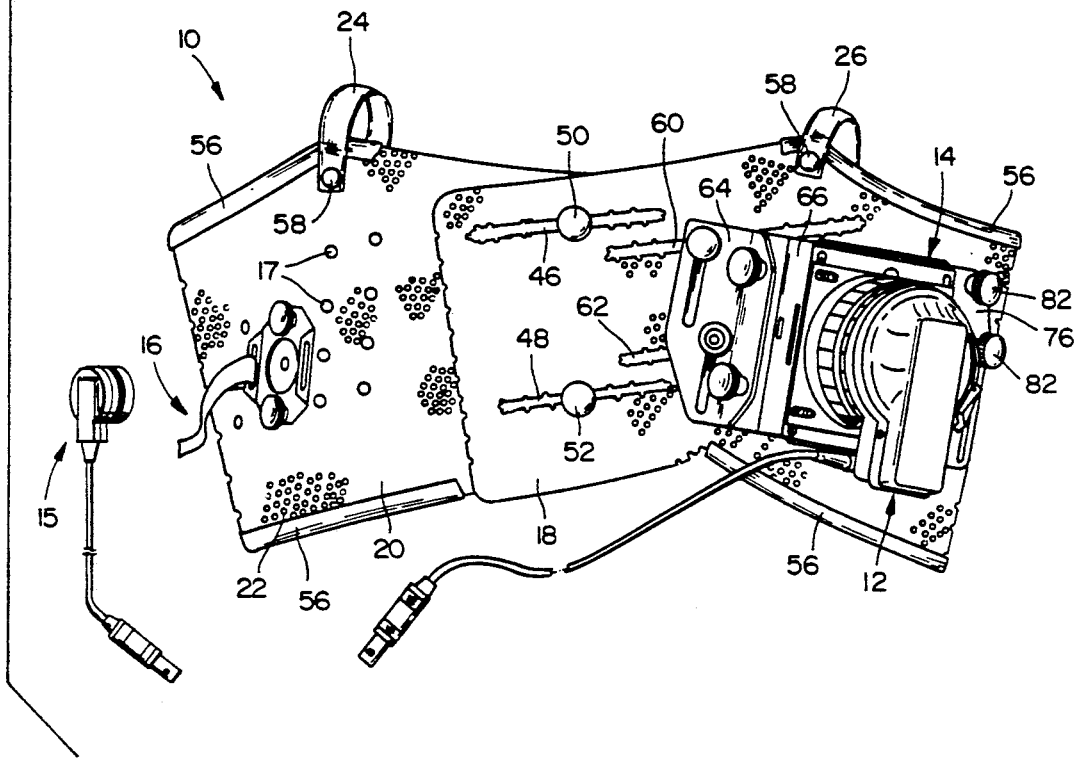
FIG. 1 is a front view of the vest for supporting the ambulatory physiological evaluation system in accordance with the present invention.
Figure 2:
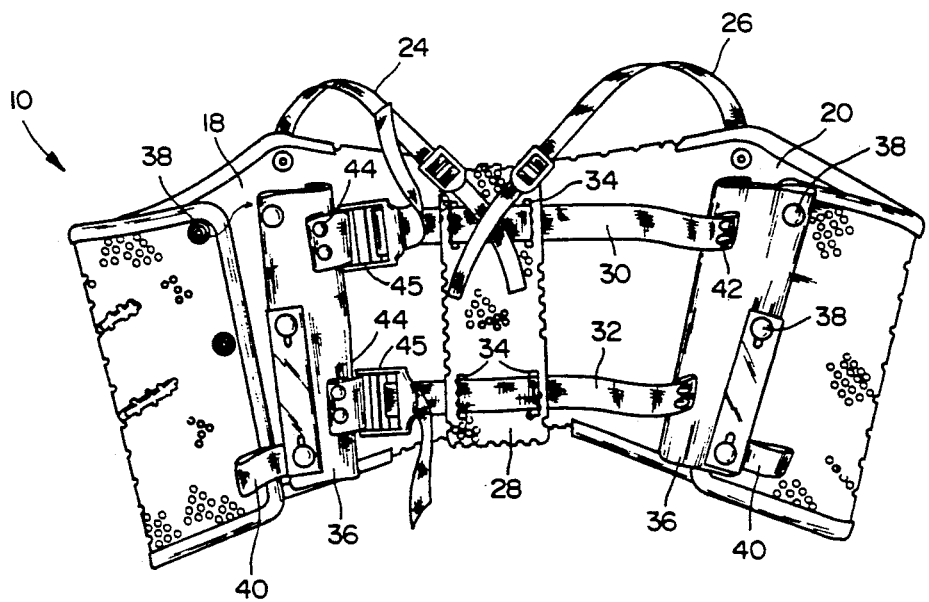
FIG. 2 is a back view of the vest illustrated in FIG. 1.
Figure 3:
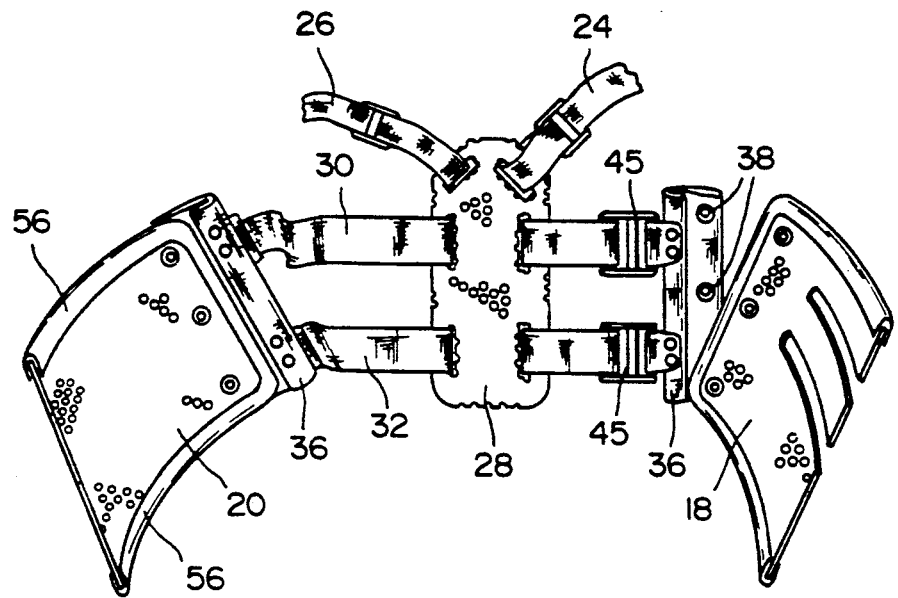
FIG. 3 is a front view of the vest illustrated in FIG. 1 having its two side members separated at the front of the vest.

Referring first to FIGS. 1-4, the ambulatory vest of the present invention will be described and is generally shown at The vest 10 is used in an ambulatory physiological evaluation system such as that disclosed in U.S. patent application Ser. No. 07/096,521, filed Sept. 15, 1987. The vest 10 supports gamma radiation detectors utilized in the nuclear medicine field for the purpose of monitoring and/or diagnosing a patient's physiological activities during a prescribed period of time. The radiation detector, shown at 12 is placed generally over the heart of a patient to sense the ebb and flow of the blood through the heart by detection of gamma rays emitted by TC-99m labeled blood cells The detector 12 is mounted onto the vest 10 by a mounting bracket assembly 14. In addition, the vest 10 includes a mounting strap assembly 16 for attaching an auxiliary radiation detector 15 to the vest 10. The mounting strap assembly 16 can be adjustably positioned on the vest by selecting two of a plurality of mounting holes 17.

The vest 10 comprises side members 18 and 20 which are separable from each other at the front and back of the vest. Each side member consists of flexible, thermal plastic material which contains a plurality of ventilation holes 22 arranged in a predetermined pattern to facilitate ventilation between the atmosphere and the skin of the wearer. In a preferred embodiment, the vest is made from a plastic material sold under the name of "Aquaplast". Shoulder straps 24 and 26 are connected to the side members 18 and 20, respectively, and connect to a vest joining member 28. The vest joining member 28 is formed of the same material as the side members 18 and 20, and connects between the side members via horizontal straps 30 and 32 which pass through slots 34 and the joining member 28. The straps 30 and 32 connect to quick release flaps 36 associated with each side member 18 and 20 of the vest 10.

The quick release flaps 36 attach to the side members 18 and 20 by snap fasteners 38. In addition, a pull tab 40 is provided for the bottom most snap to permit quick release of the flaps 36 from the side members 18 and 20. The straps 30 and 32 connect at one end to the flap 36 by snap fasteners 42. At the other end of the straps 30 and 32, there are provided strap adjustment mechanisms 45, known in the art, which attach to the flap 36 by rivets 44. The flaps 36 are made of elastic material to provide for easy adjustment and fit of the vest 10 on the patient.

Figure 4:
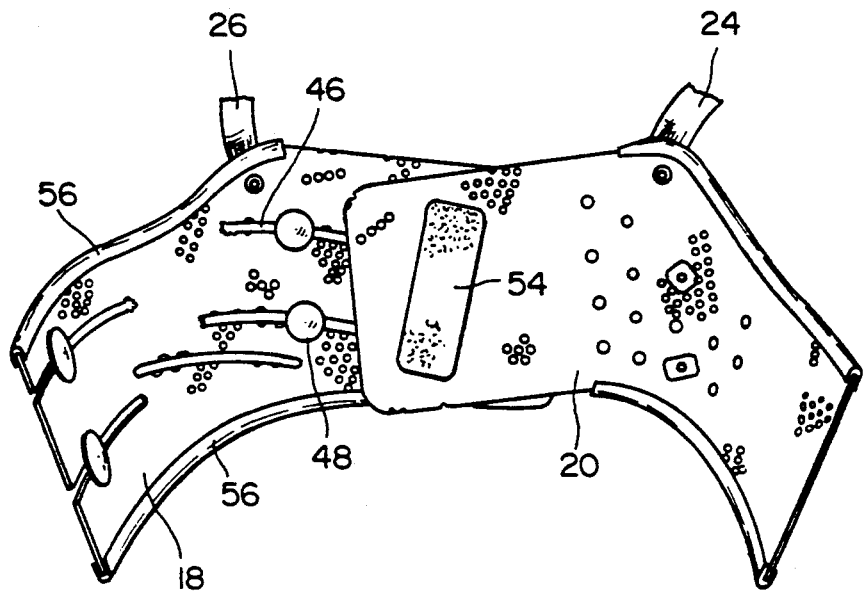
FIG. 4 is a back view of the vest illustrate in FIG. 1 having its two side members separated at the back of the vest.

At the front of the vest 10, the side members 18 and 20 have slots 46 and 48 which allow horizontal adjustment of the side members 18 and 20, relative to each other. Screw clamps 50 and 52 are provided which extend through the side members 18 and 20 via the slots 46 and 48, respectively. With the screw clamps 50 and 52 loosened, the side members 18 and 20 can slide relative to each other to allow the fit of the vest 10 to be adjusted for particular patients. As shown in FIG. 4, the screw clamps 50 and 52 attach to a pad 54 on the inside of the vest. The pad 54 tightens around the side members 18 and 20 and preferably includes a soft velvet type material which is in contact with the body of the patient.

Along the edges of the side members 18 and 20 is provided a rubber strip 56. The rubber strip 56 is glued or otherwise secured to the side members 18 and 20 and folds around the edges thereof. The purpose of the rubber strip 56 is to avoid any contact between the patient's body and the otherwise rough and uncomfortable edges of the plastic material forming the side members 18 and 20.

The straps 24 and 26 pass over the shoulders of the patient and include snap fasteners 58 similar to fasteners 38. Once adjustment of the vest 10 is completed, the straps 24 and 26 are snapped into place over the shoulders of the patient.

Figure 5:
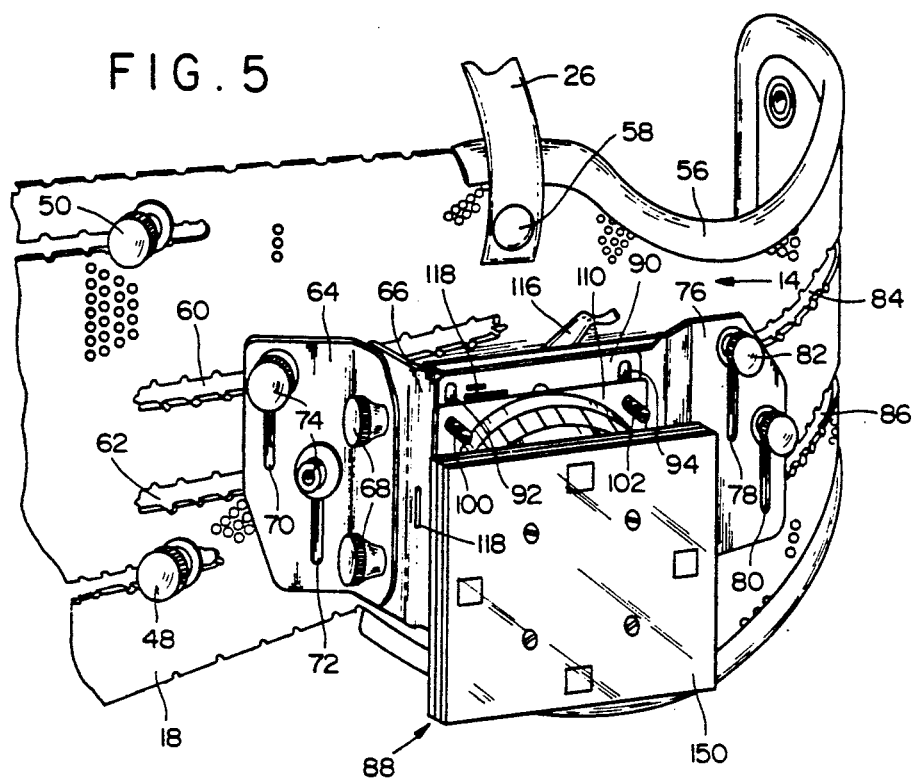
FIG. 5 is a partial front view of the vest shown in FIG. 1 and illustrating radiation detector mounting bracket with alignment fixture for the radiation detector used with the vest.

The radiation detector 12 fits onto the mounting bracket 14 which in turn attaches to the vest 10 on the front of the side member 18 as illustrated in FIGS. 1 and 5. The mounting bracket 14 fits onto the side member 18 via slots 60 and 62. Specifically, the mounting bracket 14 comprises an L-shaped flange member 64 and a front plate member 66. The flange 64 and the front plate member 66 attach to each other by screw clamps 68 which pass through aligned holes in the flange 64 and the front plate member 66.

The flange 64 has vertical slots 70 and 72 which receive screw clamps 74. The screw clamps 74 pass through the slots 60 and 62 to attach one end of the mounting bracket 14 to the vest 10. The front plate member 66 also includes an attachment portion 76 having vertical slots 78 and 80 which receive screw clamps 82. The screw clamps 82 pass through the attachment portion 76 and the slots 84 and 86 in the side member 18.

In order to get the most accurate readings from the cardiac monitor, it is imperative that the optimum position of the main detector 12 relative to the left ventricle be determined and maintained during the detecting period. Thus, as part of the present invention, a structure and method are provided for determining the exact location of the left ventricle and positioning the mounting bracket so that precise placement of the main detector 12 may be insured.

As has already been described, the main detector 12 is secured to the vest 10 through the use of a mounting bracket 14. In a preferred embodiment, the bracket is a light weight formed metallic structure. The bracket 14 may be adjustably mounted to the vest and the main detector 12 may be adjustably mounted to the bracket thus providing adjustment of the main detector 12 relative to the left ventricle of the heart within two degrees of freedom.

The mounting bracket 14 can be adjustably positioned on the vest 10 to properly align with the left ventricle of the heart of the patient. Specifically, the bracket 14 can be moved vertically via slots 70, 72, 78, and 80 and horizontally via slots 60, 62, 84, and 86 in the vest 10.

An alignment fixture is employed in order to properly align the detector mounting bracket 14 relative to the vest 10. The purpose of the fixture is to transfer a location of an anatomical body, such as the left ventricle of the heart, utilizing a conventional scintillation camera.

With reference to FIG. 5, the alignment fixture may be described as follows. The fixture basically comprises a generally square planar cursor-locating plate 88 identical to that disclosed in U.S. patent application Ser. No. 07/096,521, filed on Sept. 15, 1987, which is incorporated herein as reference.

Referring to FIG. 5–8, a further adjustment mechanism is provided for adjusting the position of the alignment fixture 88 and hence detector 12 relative to the mounting bracket 14. The L-shaped member 66 of the mounting bracket 14 includes a mounting plate 90 on the front face thereof. The mounting plate 90 has vertical slots 92, 94, 96, and 98 through which adjustment screws 100, 102, 104, and 106 pass. The adjustment screws 100–106 have pimpled surfaces to facilitate adjustment by hand, and also have a slot 107 to allow use with a tool.

A universal ball socket assembly 108 is provided which receives the alignment fixture 88 and detector 12. The ball socket assembly 108 is similar to that disclosed in U.S. patent application Ser. No. 07/096,521, filed Sept. 15, 1987. A base plate 11 is provided on the back of the socket assembly 108 which has holes to allow screws 100–106 to pass therethrough and into the slots 92-98. The screws 100–106 can be loosened to adjust the position of the ball and socket assembly 108 vertically on the mounting plate 90. Screws 112 with operating levers 114 are also provided to adjust the lateral position of the combination of the ball socket assembly 108 and the mounting plate 90, relative to the front plate member 66. The levers 114 include angled plastic shrink-on caps 116 which protrude forwardly to prevent the levers 114 from being inaccessible behind the front plate 66. Rotation of the levers 114 loosens the screws 112 and allows movement of the base mounting plate 90 relative to the front plate 66. When the levers are tightened, the screws 112 frictionally engage and hold the plate 90 secure relative to the front plate 66.

Figure 6:
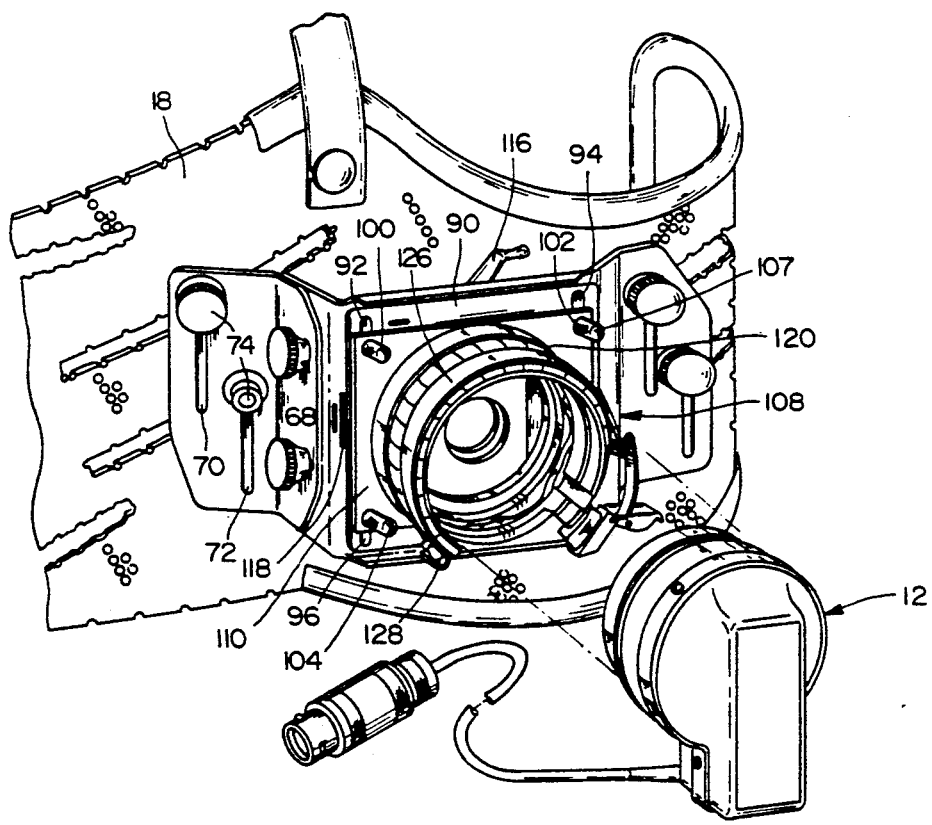
FIG. 6 is a partial front view of the vest shown in FIG. 1 and illustrating the use and mounting of a radiation detector with a radiation detector mounting bracket on the vest.

Painted or otherwise etched on the mounting plate 90 are guiding lines which are used together with the alignment fixture 88 for aligning the ball socket assembly 108 on the front plate 66. The alignment fixture 88 is used to precisely position the ball socket assembly 108 according to the procedure disclosed in U.S. patent application Ser. No. 07/096,521. Once the ball socket assembly is positioned, the radiation detector 12 is inserted therein as illustrated in FIG. 6.

Referring now to FIGS. 6-10, the ball socket assembly 108 and mounting features of the radiation detector 12 will now be described.

Figure 7:
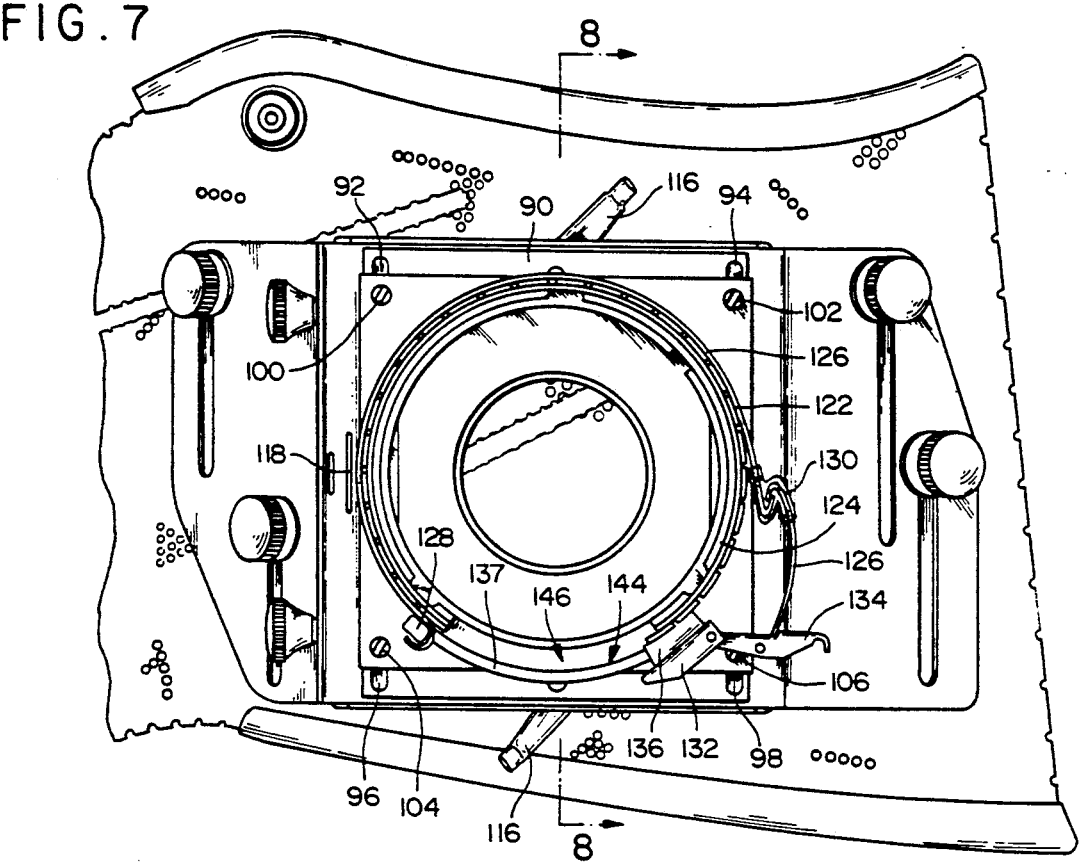
FIG. 7 is a front view of the radiation detector mounting bracket on the vest illustrated in FIG. 1.
Figure 10:
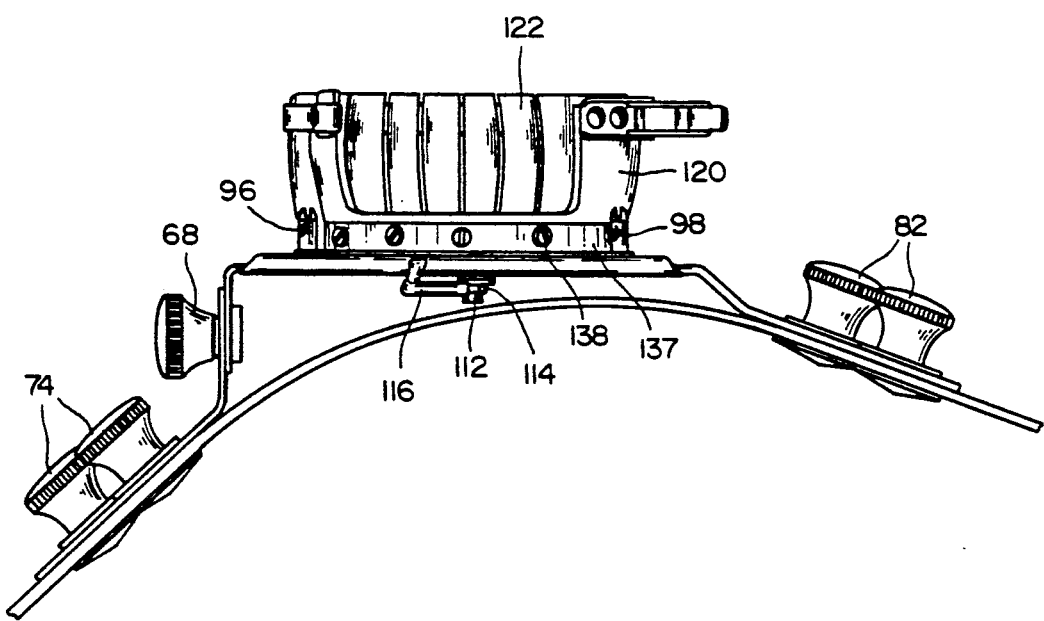
FIG. 10 is a bottom view of the radiation detector mounting bracket shown in FIG. 7.

Secured on the outer surface of base plate 110 by any suitable means such as adhesive or threaded connectors, is a ball socket support ring 120 which has a series of integrally formed forwardly extending flexible fingers 122, which extend over a circumference of about 315°-330°. The fingers 122 are somewhat concave in profile (see FIGS. 8, 9 and 10) and form a part of a cup-like retainer for a similarly profiled generally cylindrical ball socket 124 made of a hard plastic material. The flexible fingers 122 and the ball socket 124 have complimentary concave-convex, inner and outer surfaces whereby the socket 124 can swivel axially within the fingers and can also be rotated circumferentially. However, the ball socket 124 can be locked in position within the retaining fingers by a locking mechanism comprising a substantially inextensible tightening strap 126 which circumferentially surrounds the fingers 122. One end of strap 126 is fixedly secured to a fitting 128 on the exterior of ring 120, and the other end of the strap is secured to a retaining band 130, which is itself attached at a pivot connection 132 (FIG. 28) to an over-center, toggletype latching lever 134 mounted on a support 136 also carried by ring 120. The fitting 128 and support 136 are positioned on opposite ends of a support band 137. The support band 137 is formed of aluminum alloy or other suitable material, and curved to match the curvature of the ring 120 and attaches to the ring 120 via screws 139, as best illustrated in FIGS. 7 and 10. By lifting the lever 134, the strap 126 is released, loosening the grip of the fingers 122 on ball socket 124 and allowing the socket 124 to rotate and swivel. Lowering the lever 134 with an over-centering action draws the strap 126 closed, tightening the grip of the fingers 122 on the socket 124 and effectively friction-locking the socket 124 in place.

Figure 8:
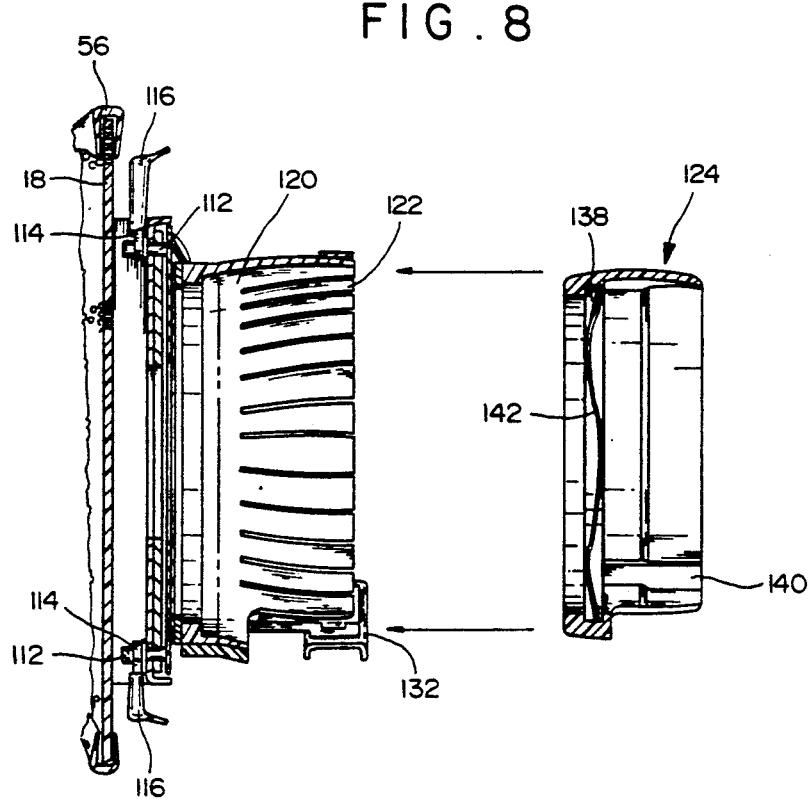
FIG. 8 is a sectional view as seen through line 8—8 in FIG. 7.
Figure 9:
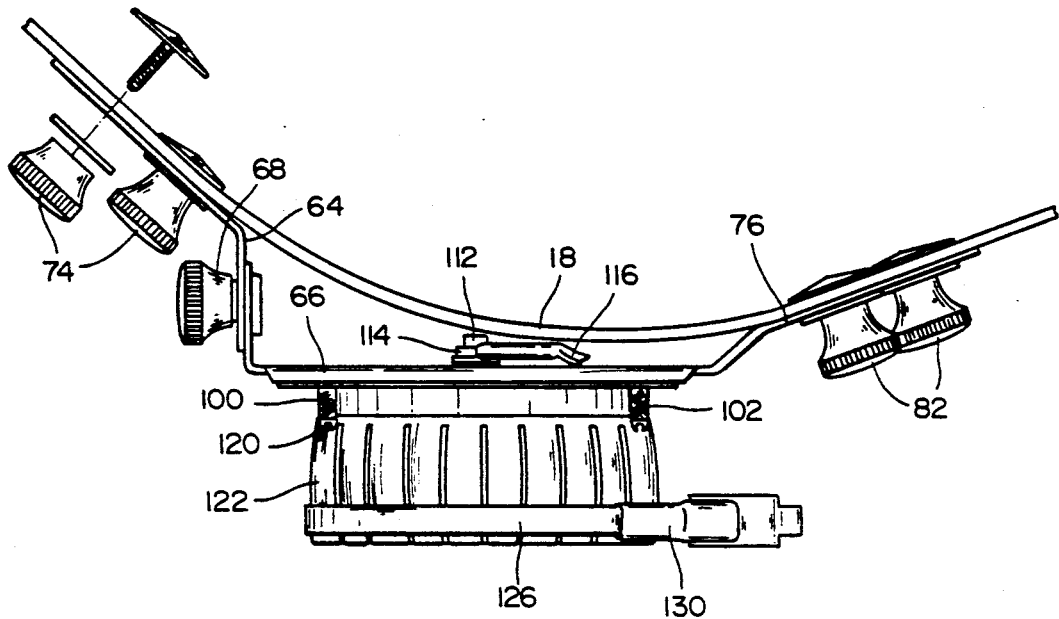
FIG. 9 is a top view of the radiation detector mounting bracket illustrated in FIG. 7.

Internally, socket 124 has a stepped profile (see particularly FIG. 8) with a circumferential rebated groove 138 toward its inner end and three equally peripherally spaced channels 140 (only one of which is shown in FIG. 8) in the inner peripheral wall of the socket leading into groove 138. A thrust washer 142 having a pre-shaped wave-like profile is located in groove 138. As previously indicated, socket 124 is adapted selectively to receive the alignment fixture 88 and the main detector 12.

Both the ring 120 and the socket 124 have cut-out portions 144 and 146, respectively, which when the socket is fitted in the ring 120 properly, align with each other and face downward, as shown in FIGS. 6 and 7.

The alignment fixture 88 (see FIG. 5) fits in the ball socket 124, and an outer plate portion 150 is provided as a datum surface for a Gamma camera as described in the previously cited patent application. Briefly, fixture 88 has a cylindrical body portion which supports a peripheral ring provided with three equally interspaced projecting tabs (not shown) to align with and engage in the previously referred to channels 140 in the socket 124. To releasably fix the fixtures in the socket, the tabs are pushed down the channels 140 until they engage and resiliently depress the thrust washer 142. Then by twisting the alignment fixture, the tabs can be moved along groove 138 out of the respective channels so that the fixture 88 is fixed in place by a bayonetting-type action. When the fixture 88 is released, the resilient thrust washer 142 holds it tightly in place. In order to remove the fixture 88 from the ball socket 124, the fixture is depressed against the thrust washer 142 so the tabs can be realigned with channels 140.

The main detector device 12 has a cylindrical body portion with projecting tabs (not shown) for engagement in the channels 140 of the ball socket 124, whereby the detector can be attached to and detached from the ball socket in like manner to the attachment and detachment of the alignment fixture.

Use and operation of the modified apparatus may be readily understood from the foregoing. It is evident that firstly, the alignment fixture will be inserted in the ball socket, and used in conjunction with a Gamma camera as in the first embodiment accurately to target the patient's left ventricle, using the available adjustments of the mounting structure, namely the lateral movement available to base plates 110, the angular adjustments available in the front plate 66 and L-shaped flange 64, and the swivel adjustment available by movement of the ball socket 124. When the patient's ventricle has been accurately targeted, the various adjustment mechanisms, including strap 126 which locks the ball socket in place, are tightened down, and the alignment fixture is then replaced by the detector device.

The above description is intended by way of example only, and is not intended to limit the present invention in any way, except as set forth in the following claims.

I claim:

1. A vest for use in an ambulatory physiological evaluation system, said vest comprising:
   a chest member comprising first and second detachable side members which are detachably at the front and back of the vest, said check member shaped to cover the upper torso and the chest of a patient;
   shoulder straps connected to each of said side members for passing over each shoulder of the patient and holding the vest on the patient;
   coupling means positioned between the first and second side member at the back of the vest; and
   quick-release means connected to said coupling means for detachably connecting the coupling means to said first and second side members;
   and further comprising a plurality of slots in each of the first and second side members and the front of the vest, screw clamps passing through said slots of said first and second side members to allow positioning of said first side member relative to said second side member for adjusting the fit around the torso of the patient.

2. A vest for use in an ambulatory physiological evaluation system, said vest comprising:
   a chest member comprising first and second detachable side members which are detachable at the front and back of the vest, said chest member shaped to cover the upper torso and the chest of a patient;
   shoulder straps connected to each of said side members for passing over each shoulder of the patient and holding the vest on the patient;
   coupling means positioned between the first and second side members at the back of the vest; and
   quick-release means connectd to said coupling means for detachably connecting the coupling means to said first and second side members, wherein said quick-release means comprises first and second flaps which releasably attach to the first and second side member, respectively, adjustable length straps which pass through slots in said coupling means and attach to said first and second flaps;

and further comprising first and second pull tabs on said first and second flaps, respectively, for facilitating release of said first and second flaps from said first and second side members.

3. The vest of claim 2, wherein said first and second side members and said first and second flaps have snap fasteners to releasably attach to each other, respectively.

4. A vest for use in an ambulatory physiological evaluation system, said vest comprising:
- a chest member containing first and second detachable side members which are detachable at the front and back of the vest, said chest member shaped to cover the upper torso and the chest of a patient;
- shoulder straps connected to each of said side members for passing over each shoulder of the patient and holding the vest on the patient;
- coupling means positioned between teh first and second side members at the back of the vest; and
- quick-release means connected to said coupling means for detachably connecting the coupling means to said first and second side members;
- wherien one fo said first and second side members has parallel slots on the front portion thereof for receiving a radiation detector mounting bracket assembly, said assembly capable of being adjustably positioned on said vest in said slots.

5. A vest for use in an ambulatory physiological evaluation system, said vest comprising:
- a chest member comprising first and second detachable side members which are detachable at the front and back of the vest, said chest member shaped to cover the upper torso and the chest of a patient;
- shoulder straps connected to each of said side members for passing over each shoulder of the patient and holding the vest on the patient;
- coupling means positioned between the first and second side members at the back of the vest; and
- quick-release means connected to said coupling means for detachably connecting the coupling means to said first and second side members;
- and further comprising a plurality of openings in one of said first and second side members to expose the skin of the patient for receiving ECG electrodes.

6. A vest for use in an ambulatory physiological evaluation system, said vest comprising:
- a chest member comprising first and second detachable side members which are detachable at the front and back of the vest, said chest member shaped to cover the upper torso and the chest of a patient;
- shoulder straps connected to each of asid side members for passing over each shoulder of the patient and holding the vest on the patient;
- coupling means positioned between the first and second side members at the back of the vest; and
- quick-release means connected to said coupling means for detachably connecting the coupling means to said first and second side members;
- and further comprising rubber stripping along the peripheral edges of said first and second side members.

7. A vest for use in an ambulatory physiological evaluation system, said vest comprising:
- a chest member comprising first and second detachably side members which are detachably at the front and back of the vest, said chest member shaped to cover the upper torso and the chest of a patient, wherein said chest member is formed of plastic material having a plurality of ventilation apertures;
- shoulder straps connected to each of said side members for passing over each shoulder of the patient and holding the vest on the patient;
- coupling means positioned between the first and second side members at the back of the vest, wherein said coupling means is formed of plastic material having a plurality of ventilation holes; and
- quick-release means connected to said coupling means for detachably connecting the coupling means to said first and second side members.

* * * * *